United States Patent [19]
Deslauriers

[11] Patent Number: 5,952,618
[45] Date of Patent: Sep. 14, 1999

[54] ACOUSTIC CONDUIT FOR USE WITH A STETHOSCOPE

[76] Inventor: Richard J. Deslauriers, 78 Joseph St., Waterbury, Conn. 06705

[21] Appl. No.: 09/106,259

[22] Filed: Jun. 29, 1998

Related U.S. Application Data

[63] Continuation-in-part of application No. 08/680,274, Jul. 11, 1996, Pat. No. 5,774,563.
[51] Int. Cl.[6] ...................................................... A61B 7/02
[52] U.S. Cl. ........................................... 181/131; 181/137
[58] Field of Search ..................... 181/131, 137; 381/67

[56] References Cited

U.S. PATENT DOCUMENTS

| | | |
|---|---|---|
| 3,772,478 | 11/1973 | McCabe et al. ......................... 181/131 |
| 4,071,694 | 1/1978 | Pfeiffer . |
| 4,200,169 | 4/1980 | MacDonald, III et al. ............ 181/131 |
| 4,270,627 | 6/1981 | Hill ........................................ 181/131 |

*Primary Examiner*—Khanh Dang
*Attorney, Agent, or Firm*—Baker & Botts, L.L.P.

[57] ABSTRACT

An acoustic conduit includes an outer tube and two independent inner tubes. The outer tube is formed of a first material having a first density. The inner tubes are formed of springs of a second material having a second density and each creates an acoustic chamber. The first and second materials are chosen so that the second density is greater than the first density. The acoustic conduit may be used as, for example, a stethoscope tube.

11 Claims, 18 Drawing Sheets

ELECTRONIC CIRCUITRY

METHOD OF ASSEMBLING STETOSCOPE

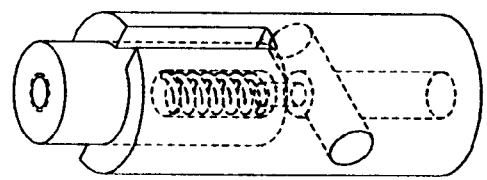
FIGURE 10-B
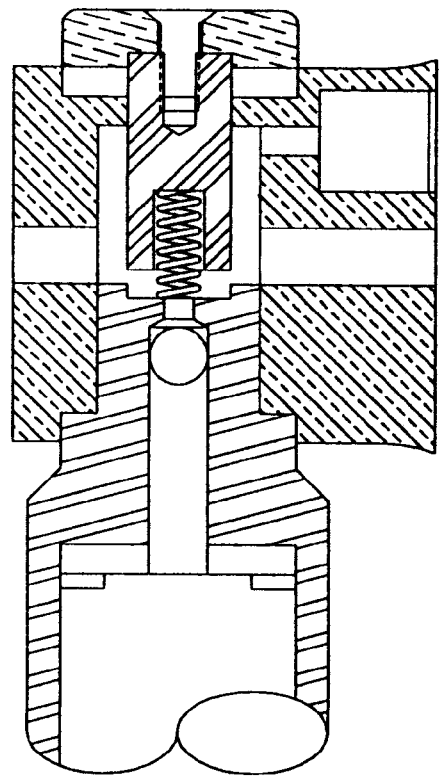
FIGURE 10-A

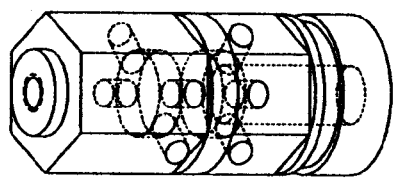
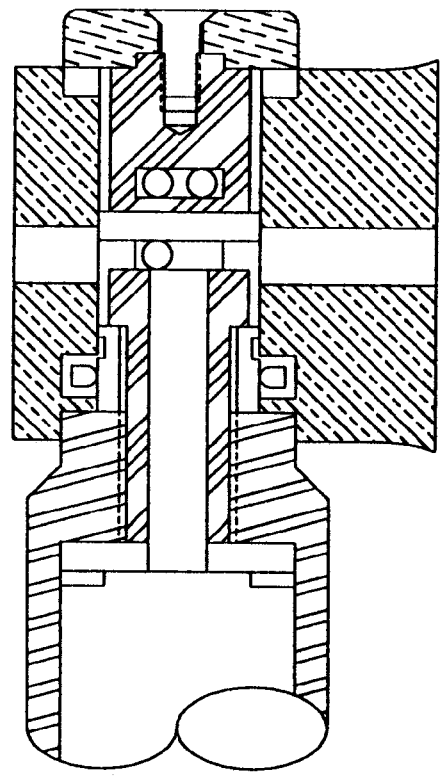

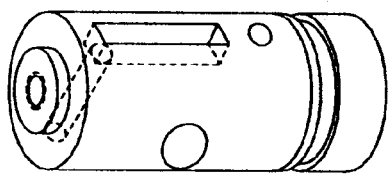
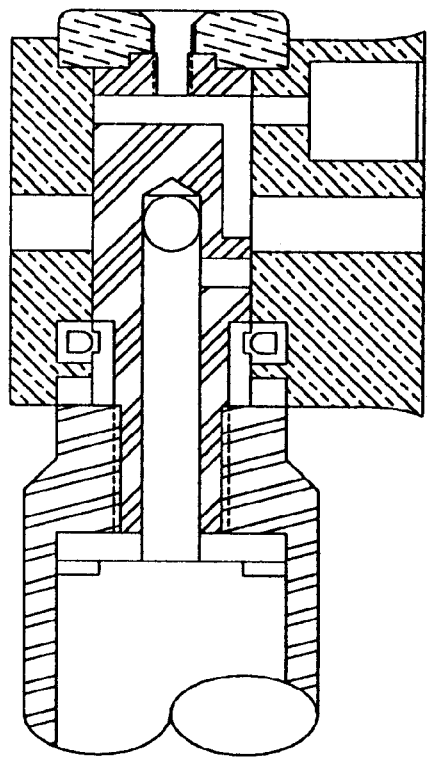

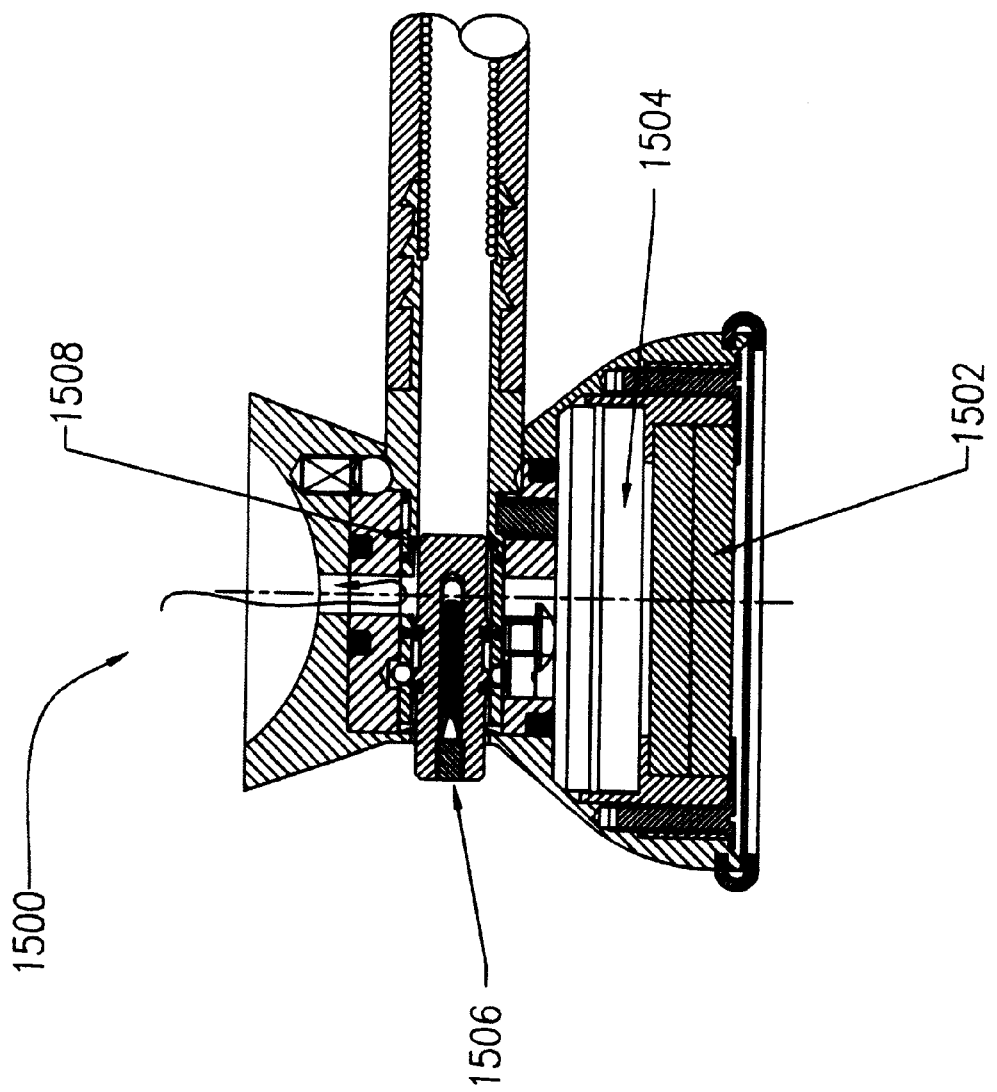

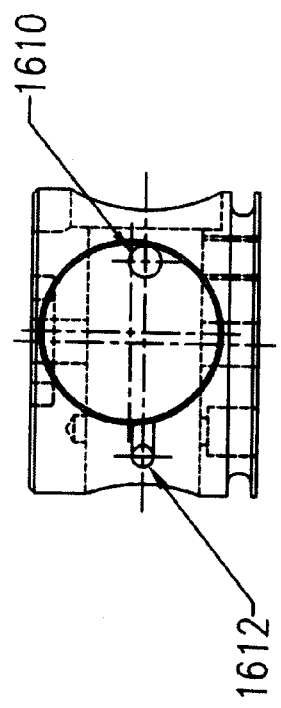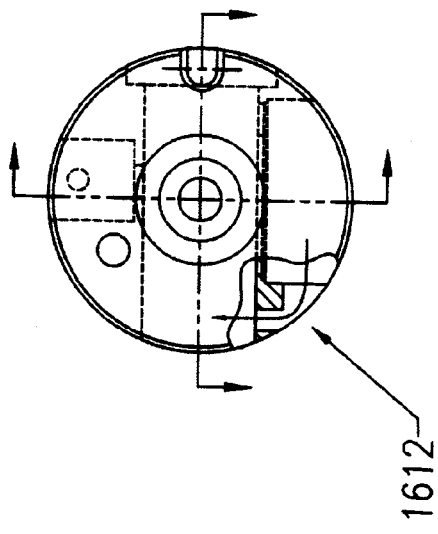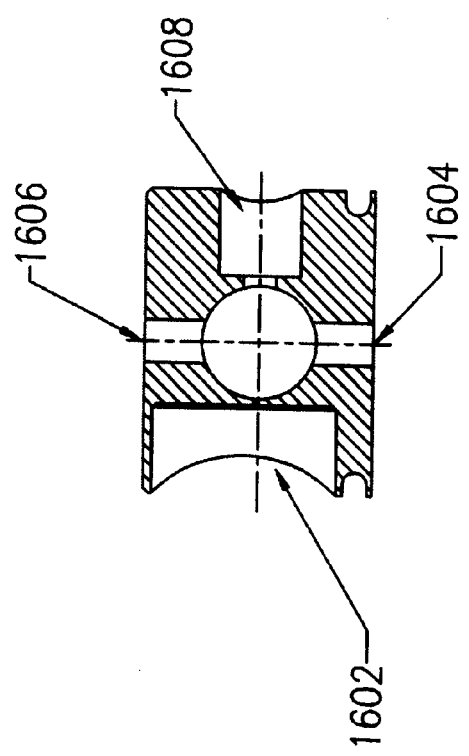

(1)

ACOUSTIC CONDUIT FOR USE WITH A STETHOSCOPE

This application is a CIP of 08/680,274, filed Jul. 11, 1996, now U.S. Pat. No. 5,774,563.

FIELD OF THE INVENTION

This invention relates to diagnostic auscultation. In particular, the invention relates to a new design for an acoustic conduit for use with, for example, a combined electronic acoustical stethoscope for recording and amplifying sounds produced by body structures.

BACKGROUND OF THE INVENTION

Auscultation has long been a very useful tool for medical diagnosis of ailments. By using a stethoscope, health care providers can listen and identify sounds associated with abnormalities. The most common of these are heart murmurs which, when properly identified, indicate specific abnormalities in the function of the heart. Identifying specific murmurs, like identifying heart sounds, is difficult. Developing the skills necessary to make a proper analysis takes years of study and practice. Since many heart murmurs are rare or seldom encountered by the general physician or medical students, expertise is never acquired.

Furthermore, most body sounds fall either just at or below the audible frequency range of the human ear. Therefore, even with years of experience, the ability of a physician to perform an accurate diagnosis is limited by the fact that conventional stethoscopes do not have adequate audio resolution. This inadequacy is caused by a number of factors. One significant cause is the tube or conduit connecting the housing to the ear pieces. In a conventional stethoscope this conduit is generally a single acoustic chamber formed by the inner diameter of a flexible tube. This conventional structure has drawbacks in that it does not permit maintenance of separate channels for the left and right ears. Further, this conventional structure is susceptible to interference from external noise caused by physical contact.

Modem electronic stethoscopes can improve sound quality and provide visual indication of heart sounds or chest sounds. However, these electronic stethoscopes are more expensive and bulkier than conventional stethoscopes and typically require significant external electronics to operate. Moreover, the performance of these modem stethoscopes is typically also limited by the structure of the conduit connecting the housing and ear pieces.

SUMMARY OF THE INVENTION

An object of this invention is to overcome the problems and disadvantages associated with current strategies and designs and provide novel electronic stethoscope features for diagnostic auscultation.

Another object of the present invention is to provide an acoustic conduit having a structure that minimizes external noise interference.

Another object of the invention is to provide an acoustic conduit having a structure that promotes self straightening and decreases the likelihood of the conduit kinking.

One embodiment of the invention is directed to a stethoscope that receives and records a body sound while maintaining the standard stethoscope features. The stethoscope comprises a head with a bell end and a diaphragm end. The stethoscope contains a microphone, electronic circuits, a speaker, digital recording circuits and a means of eliminating acoustic feedback.

Another embodiment of the invention is directed to a method for amplifying and recording a body sound with a stethoscope. This method comprises placing a head of the stethoscope against a surface of a body. The body sound is detected by a microphone within the head of the stethoscope and processed. Body sounds are stored in a digital recording circuit for playback.

Another embodiment of the invention is directed to a method for assembling a stethoscope that receives and records a body sound. The stethoscope is assembled by attaching a stethoscope head, that contains electronics (recording circuit, microphone, speaker, amplifier) to an elastic tube which connects the head to the ear pieces.

In another embodiment, the invention is directed to a stethoscope comprising a head assembly, a conduit assembly and a first and a second ear piece. The conduit assembly has a proximal end connected to the head assembly and a distal end connected to the first and second ear pieces. The conduit assembly comprises a flexible outer tube comprised of a first material having a first density. A first inner tube is independent from and disposed within the outer tube. The first inner tube is comprised of a second material having a density greater than the first density. A second inner tube is independent from and disposed within the outer tube. The second inner tube is also comprised of the second material. The first inner tube and the second inner tube define a first acoustic chamber and a second acoustic chamber respectively.

In another embodiment the invention is directed to a flexible acoustic conduit used to transmit sound from a source to a destination through a first acoustic chamber and a second acoustic chamber. The conduit comprises a flexible sheath comprised of a first material, that encases the first acoustic chamber and the second acoustic chamber. A first inner spring disposed within the flexible sheath forms the first acoustic chamber, and a second inner spring disposed within the flexible sheath forms the second acoustic chamber.

Other objects and advantages of the invention are set forth, in part, in the description which follows and, in part, will be obvious from this description, or may be gleaned from the practice of the invention.

BRIEF DESCRIPTION OF THE DRAWINGS

FIG. 10-A A cross-sectional view of the spool plunger isolator according to one embodiment of the present invention.

FIG. 10-B A pictorial view of the spool plunger isolator according to one embodiment of the present invention.

FIG. 11-A A cross-sectional view of the spool hex isolator according to one embodiment of the present invention.

FIG. 11-B A pictorial view of the spool hex isolator according to one embodiment of the present invention.

FIG. 12-A A cross-sectional view of the spool slot isolator according to one embodiment of the present invention.

FIG. 12-B A pictorial view of the spool slot isolator according to one embodiment of the present invention.

FIG. 13-B A cross-sectional view of the spool according to one embodiment of the present invention.

DETAILED DESCRIPTION OF THE PREFERRED EMBODIMENTS

Figure 1:
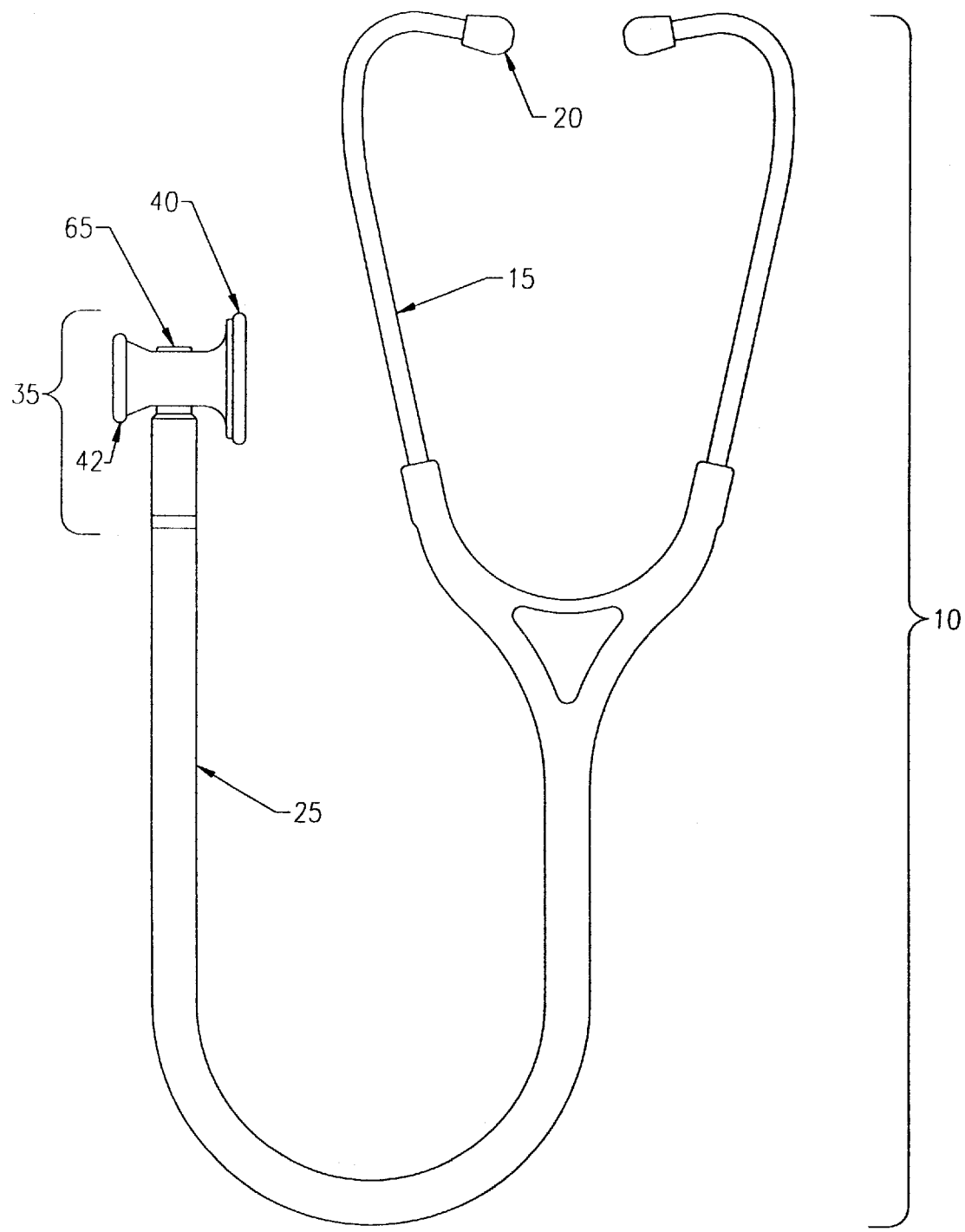
FIG. 1 A pictorial view of one embodiment of the present invention.

As embodied and broadly described herein, the present invention is directed to novel electronic stethoscopes for diagnostic auscultation of body structures.

Conventional stethoscopes are designed to detect sounds produced in the body. A conventional stethoscope contains ear pieces connected to the bell/diaphragm by a flexible tube for receiving sound. This stethoscope is generally satisfactory and reliable but its simplicity is also a significant disadvantage as many physiological sounds are reproduced without sufficient clarity to perform rapid and accurate diagnosis of the physiological precursor of the sound.

The present invention comprises a conventional stethoscope and one that incorporates amplification and/or recording circuits possible with today's electronics. Electronic stethoscopes have been proposed to modify the physiological signal to produce an audible signal which has clarity and which more accurately reflects the original physiological sound. Some advantages and disadvantages of several such electronic stethoscopes are described in U.S. Pat. No. 4,528, 689. In such stethoscopes, diagnostic resolution is improved, treatment and intervention techniques can be better assessed and there is minimal patient inconvenience. Many health care providers are accustomed to the conventional stethoscope and find electronic stethoscopes expensive, cumbersome, and difficult to use. However, the preferred embodiment of the present invention, the Echo+™ stethoscope, maintains all the classic features of a conventional stethoscope. In addition, the unit is capable of automatically adjusting the intensity of the auscultated sounds to optimize proper analysis by the user. The unit also captures (records) auscultated sounds which can then be replayed. These recorded sounds, can be replayed in one of two modes. The first mode reproduces the sounds just as recorded, thus allowing repeated analysis by several users. The second mode plays the recorded sounds back at a reduced rate, thus optimizing their analysis. The recording feature of the Echo+™ is especially useful when examining easily distressed patients such as the crying neonate. By capturing the auscultated sounds before the patient becomes irritated a more accurate analysis can be performed.

The recording feature offered by the Echo+™ also provides a practical and convenient method of assessing patient progress. By comparing pre-treatment and post-treatment auscultated sounds the Echo+™ can be used to gauge the success of treatment. In the teaching setting, the advantages for the student and patient are obvious. Students can replay the auscultated sounds over and over without repeatedly reexamining the same patient, thus minimizing patient inconvenience. Additional advantages offered by the Echo+™ stethoscope include transferring of information for consultation, capturing the most appropriate auscultation environment, maintaining the familiar classic features, improved murmur detection and analysis.

In addition to the above, the Echo+™ offers improved conventional stethoscope resolution through improved acoustic chambers. A flexible metal conduit connects the housing to the ear pieces while maintaining a superior acoustic chamber. This conduit also maximizes external noise isolation and promotes self straightening and anti-kinking kinking properties. The ear pieces have also been redesigned for better fit and longer useful life.

In the following detailed description of the preferred embodiment, reference is made to the accompanying drawings which form a part hereof, and which show by way of illustration, specific embodiments in which the invention may be practiced. The embodiments are described in sufficient detail to enable those skilled in the art to practice the invention, and it is to be understood that other embodiments may be utilized and that structural changes may be made without departing from the scope of the present invention.

Specific embodiments of the present invention are described in accordance with FIGS. 1–12. One preferred embodiment of the present invention looks substantially like a conventional stethoscope externally. Construction of main body 35 is well-known to those of ordinary skill in the art. In a preferred embodiment, locking ring/tensioner 44 is constructed of stainless steel. Diaphragm plate 41 is preferably a standard epoxy diaphragm plate used in most new stethoscopes. Bell thermal isolator 42 and diaphragm thermal isolator 43 consist of a rubber ring stretched or molded over the stainless steel housing 80 and are used to decrease thermal conduction and maintain a seal with main body 35. Main body 35 is constructed from medical grade stainless steel and may be of standard construction which is well-known in the art. Bell communication port 86 and diaphragm communication port 87 are circular holes in the main body positioned 180 degrees apart and are a standard part of the main body of many conventional stethoscopes. Spool socket 88 is preferably a circular hole into which spool 90 may be housed.

Microphone 205 is preferably an omni-directional electret condenser microphone element. Speaker 210 is preferably a standard miniature communications speaker. Electrical rotating connectors 400 are constructed of a nylon outer insulator 410 and brass conductors 420. Battery holder 110 is designed to hold battery 115, preferably a 6V lithium battery. Anti-twisting device 125 preferably consists of two independent stainless steel tubes and a rubber O-ring. Stethoscope tube 25 (acoustic conduit) preferably comprises a bitumen (14"–16") neoprene tube with internal acoustic chambers 251. Neoprene is used to eliminate cracking and age induced stiffness related to use of conventional PVC and latex tubing. Acoustic chambers 251 are used to improve the acoustic chamber and to maximize external noise isolation. Acoustic chambers 251 are preferably stainless steel and may be formed by a stainless steel compression spring. This improved tube structure is explained in detail below in conjunction with FIGS. 2 and 3.

Locking ring/tensioner 44 is constructed in such a way that it mates by screws or other suitable joining method to main body 35 and secures diaphragm 41 to main body 35 while maintaining a seal with the body 35. Locking ring/tensioner 44 increases or decreases the tension applied to the diaphragm plate 41 thus proportionally changing the resonant frequency of (or tuning) diaphragm plate 41. The locking ring/tensioner 44 also houses diaphragm thermal isolator 43 (which is a non-conductive rubber ring) to decrease thermal conduction transferred to the body. Bell thermal isolator 42 and diaphragm thermal isolator 43 are used to decrease thermal conduction and maintain a seal with the body.

The main body of the stethoscope is constructed from medical grade stainless steel and houses bell communication port 86 and diaphragm communication port 87, spool socket 88, microphone 205, speaker 210, electrical rotating connections 400 and electronics 200. It should be understood that these components correspond to a particular embodiment of the present invention and other components may be substituted within the scope of the present invention. Bell communication port 86 and diaphragm communication port 87, are selected by the user by rotating spool 90, and are positioned to provide through communication (e.g. a continuous air space) with the ear pieces 20 when in the conventional mode. In a preferred embodiment of the present invention the spool rotates independent of depression and release of spool 90. The diaphragm communication port 87 is in communication with microphone 205 when in the electronic mode. Spool socket 88 houses a stainless steel spring 70 and stainless steel ball bearing 67, which are used to lock the spool 90 into bell communication port 86 or diaphragm communication port 87. Bell communication port 86 or diaphragm communication port 87 are 180 degrees apart. Microphone 205 communicates with bell communication port 86 or diaphragm communication port 87 and provides input to the electronics. Speaker 210 is a standard miniature communications speaker that communicates directly with the user's ear canal when the user selects the electronic mode. Electrical rotating connectors 400 function as: 1) an on/off switch; and, 2) a connection between battery 115, housed in the battery holder 110, and the electronics 200 housed in main body 35.

The smart switch comprises the spool 90 and the electronics 200. When the spool is depressed the housing 35 and spool brass conductors 420 are aligned (making contact), which actuates the smart switch. If the connection is broken, without reconnecting within a few milliseconds, the unit returns to the conventional mode(off). If the connection is momentarily broken, i.e., depressing spool 90 two or three times in a row, the smart switch interprets the signal and selects the appropriate response (amplify/record, playback, slow playback).

Figure 8:
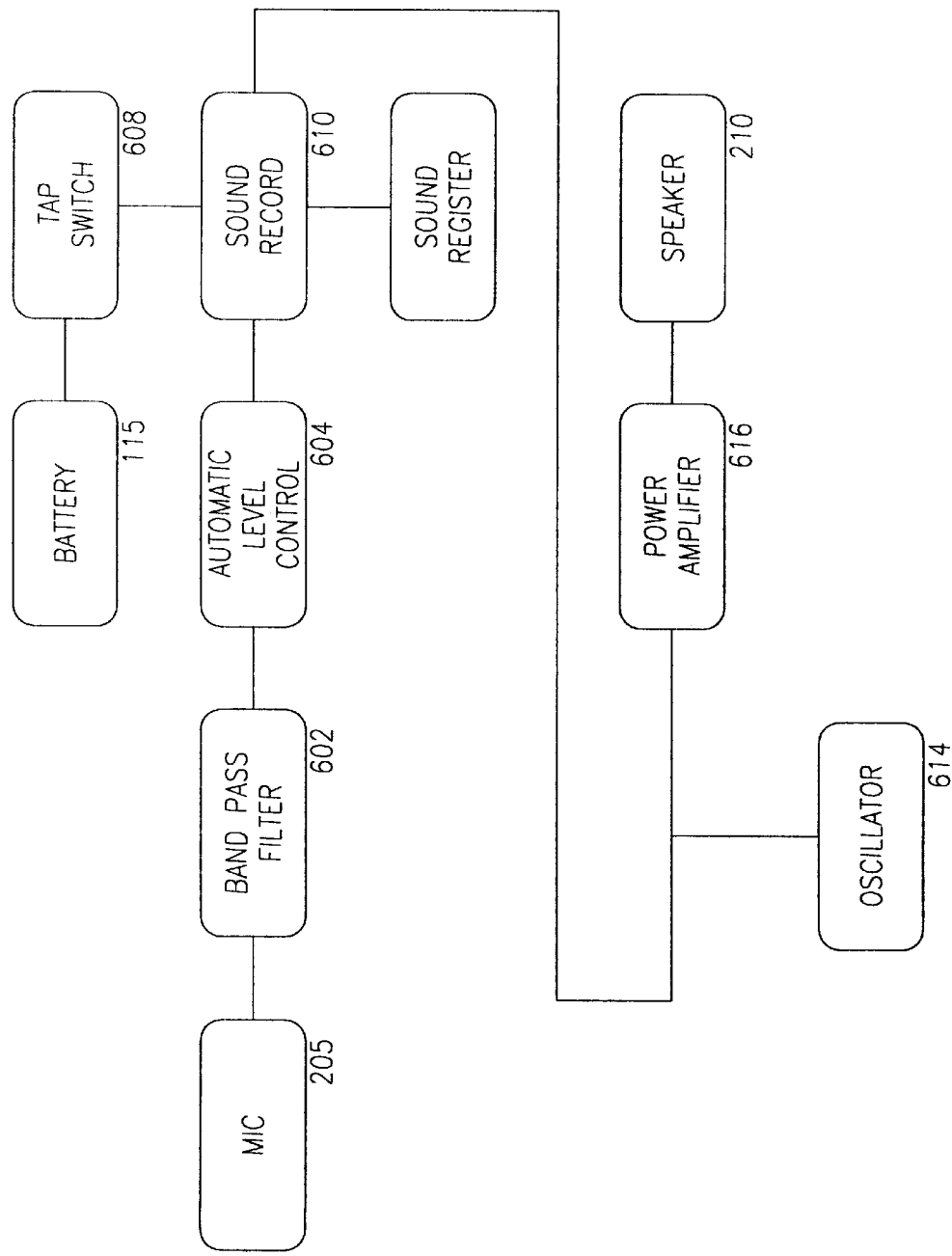
FIG. 8 A block diagram of the electronic circuitry according to one embodiment of the present invention.

FIG. 8 depicts one embodiment of electronic circuitry consisting of microphone 205, speaker 210, battery 115, and various electronic components. Electronics consist of band pass filter 602, automatic level control 604, sound recorder/sound register 610, tap switch 608, oscillator 614, and power amplifier 616. Electronics 200 (FIG. 5) are mounted and held in the stethoscope diaphragm. Band pass filer 602 limits the frequency of the signal from microphone 205 to a low pass of 70 Hz and a high pass of 480 Hz. Automatic level control 604 takes a given range of input signals and provides a constant level of AC output. Thus, a weak and strong heart will sound similar in amplitude. Sound recorder/sound register 610 is a standard sound recording circuit which can record sounds and play them back at variable speeds including normal speed. Sound recorder/sound register 610, in a preferred embodiment, has a storage capacity of 1,048,576 words×1 bit. Thus the worst case record time is approximately 14 seconds. Oscillator 614 generates a beep each time tap switch 608 is activated (e.g., positive position feedback). Power amplifier 616 increases the drive of the input signal such that it can drive speaker 210. Tap switch 608 decodes a series of activations (taps) into functions including amplified playback, and record. Tap switch 608 also controls the power to the other blocks in such a way as to save power (e.g., recorder is not powered up when in amplify mode).

Figure 4:
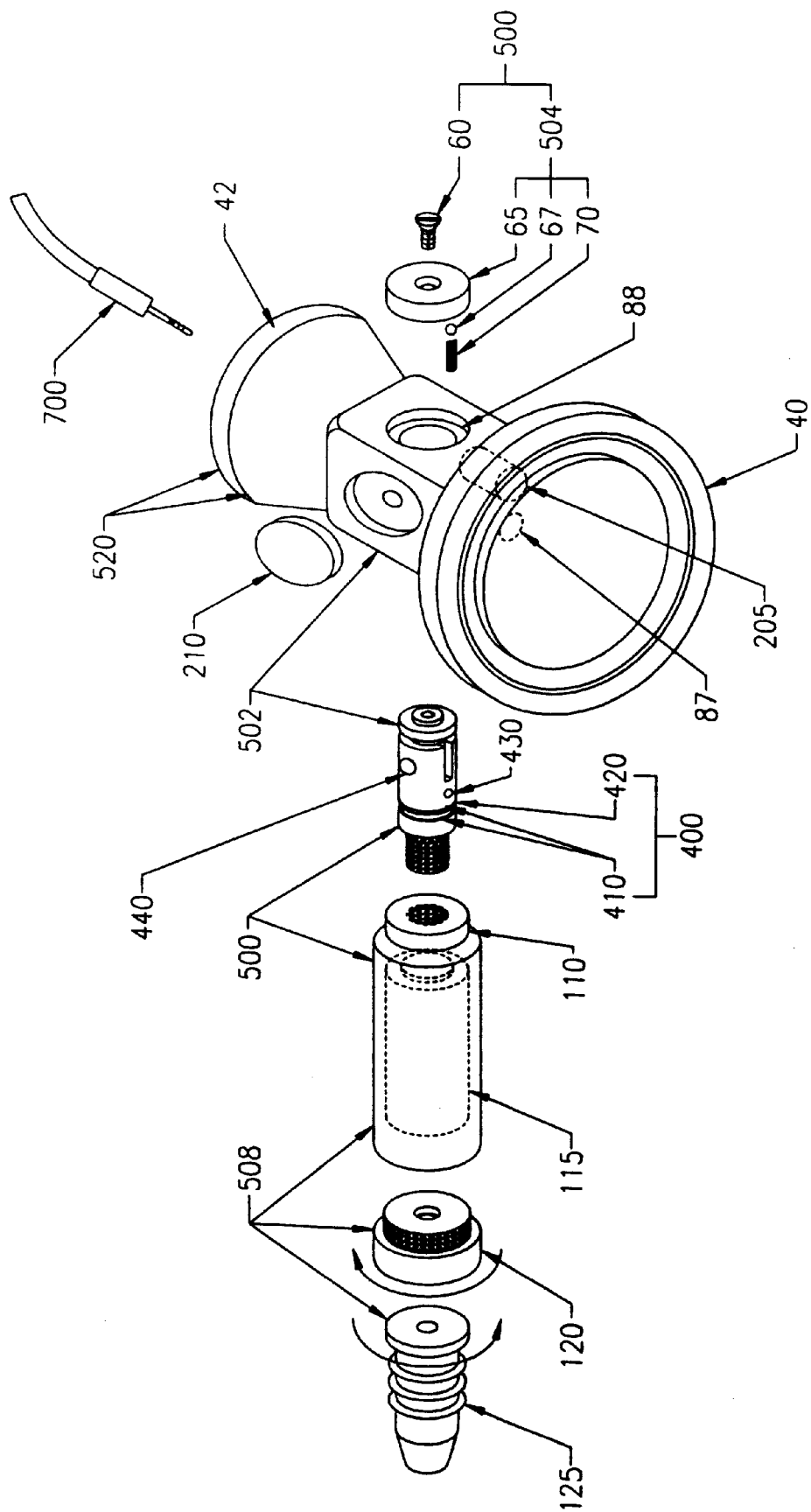
FIG. 4 A pictorial view representing a method of constructing a combined electronic/acoustic stethoscope according to one embodiment of the present invention.
Figure 5:
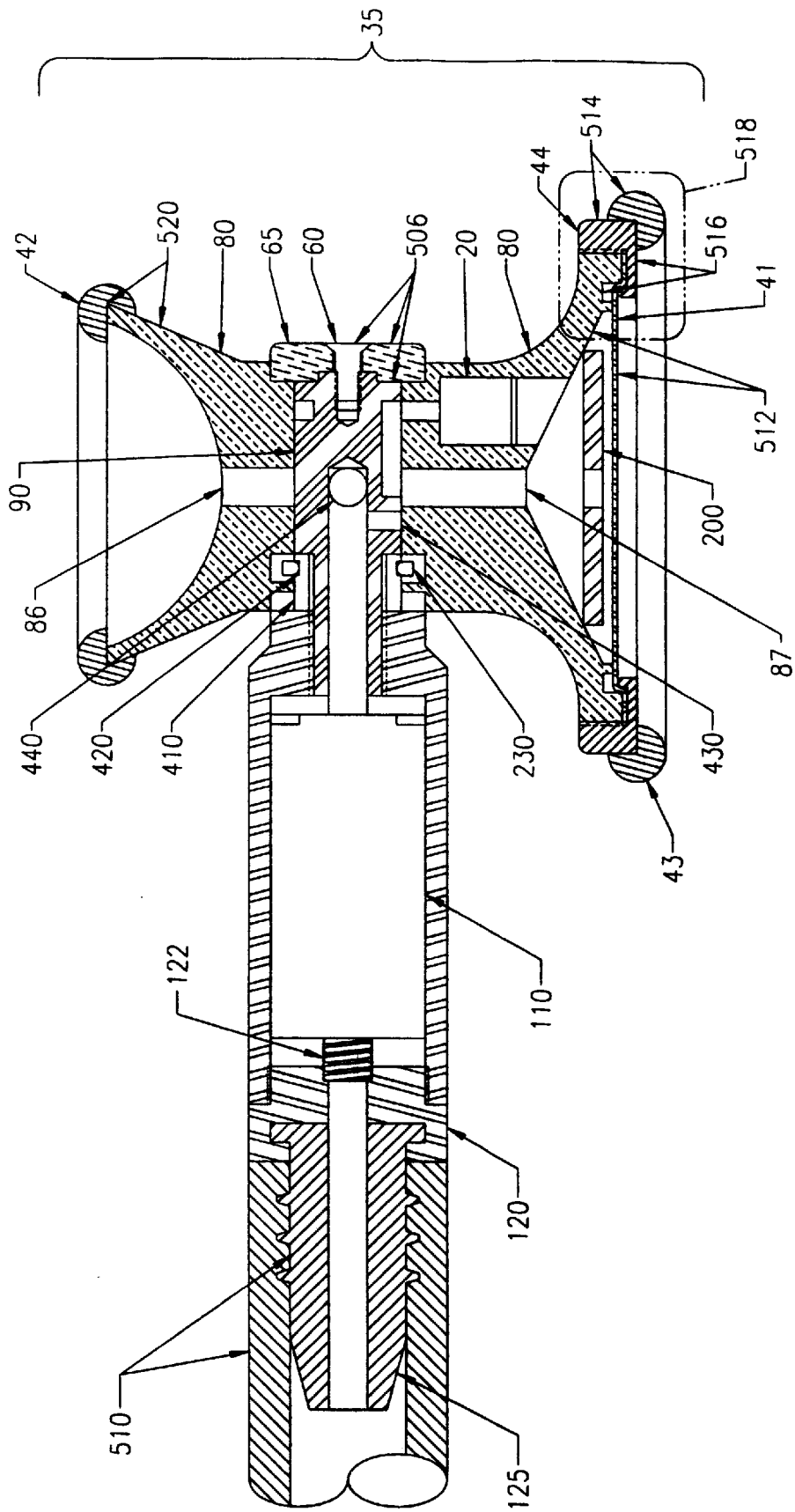
FIG. 5 A cross-sectional view of the stethoscope according to one embodiment of the present invention in electronic mode.
Figure 6:
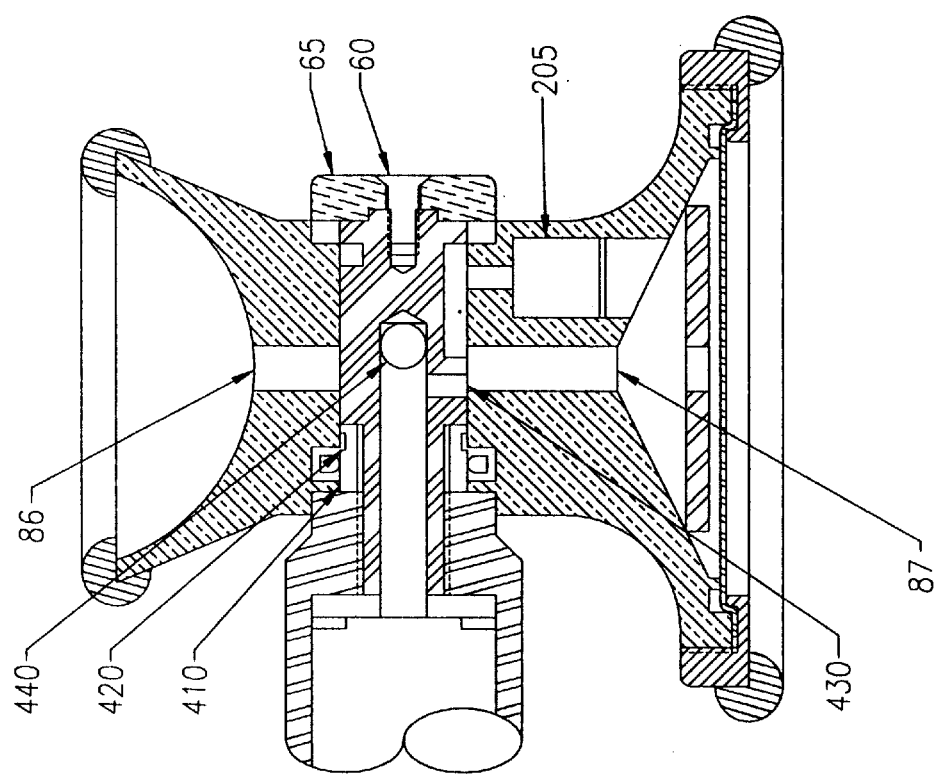
FIG. 6 A cross-sectional view of the stethoscope according to one embodiment of the present invention in conventional mode.

Referring to FIGS. 4–7, the actuator spool 90 houses the through spool port 430, washer 65, screw 60, battery 115, spring 122 and rotating electrical connectors 400, battery retaining cap 120, speaker output 440, and anti-twisting device 125. Spool 90 may contain other components and remain within the scope of the present invention. Through spool port 430 is positioned in such a way that when spool 90 is in the conventional mode, direct connection with the earpieces 20 exist. A female communication port (e.g., a quick connect female outputjack 411) is incorporated into through spool port 86. In one embodiment, the female communication port may be used to download internally stored data to an external device. Quick connect male output jack 700 provides a means of coupling the output of the stethoscope to an external device. When in the electronic mode (FIG. 5), the diaphragm communication port 87 is in communication with microphone 205. Speaker 210 is separated from the microphone 200, thus eliminating feedback, while maintaining a connection with the ear pieces. Battery holder 110 is designed to hold a 6V lithium battery and maintain a patent air canal. Battery holder 110 is shaped such that air can pass in the axial direction between battery holder 110 and main body 35. The user's ear canal is continuous with the air canal between the inside of the main body and the ear pieces. The user's ear canal is continuous with the speaker 210 in the electronic mode (FIG. 5). In the conventional mode, the user's ear canal is continuous with bell communication port 86 when using the bell and diaphragm communication port 87 when using the diaphragm (FIG. 6). A stainless steel spring 122, connected to the anti-twisting device 125, provides a compression force to hold the battery 110 into position. Anti-twisting device 125 preferably consists of two independent stainless steel tubes and a rubber O-ring constructed in such a manner that they can rotate independently while maintaining an air seal.

In addition to the preferred actuator, i.e., spool 90, several different versions have been developed. Referring to FIGS. 10a and b, in the first alternative embodiment, a spool plunger isolator separates microphone 205 from speaker 210 and ear canal while maintaining a through connection with microphone 205. The through connection is selected by rotating spool 90 by 180 degrees. When the plunger is depressed it closes the ear canal through port and eliminates feedback. When released the ear canal through port is free to communicate with the selected port. As with spool 90, rotating the ear canal through port 180 degrees selects the bell communication port 86 or diaphragm communication port 87.

In the second alternative embodiment, a spool hex isolator (FIGS. 11a and b) separates microphone 205 from speaker 210 and ear canal while maintaining a through connection for microphone 205. The spool hex isolator consist of a hex with a distal blind hole and a proximal hole that connects with the tube. Direct connection between the blind port is through one side only. Depressing the actuator breaks the direct connection, thus isolating speaker 210 and microphone 205. Releasing the spool reestablishes communication between the ear canal and selected port. The remaining sides of the proximal hex port are used to provide a speaker through hole with the ear canal when in the bell or diaphragm mode. The remaining sides of the distal hex port are used to maintain a through hole with microphone 205 and selected port. Rotating the spool 180 degrees selects the opposite port.

Figure 7:
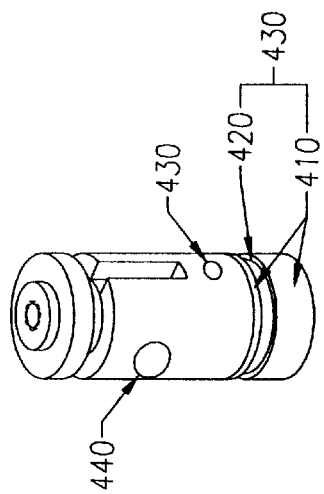
FIG. 7 A pictorial view of the spool according to one embodiment of the present invention.

In the third alternative embodiment of actuator, a fully automatic spool utilizing a miniature electric valve to separate the ports has been developed. This configuration eliminates the need to depress the spool to isolate various ports. When the electric valve is energized, speaker 210 and microphone 205 are separated while microphone 205 maintains communication with the selected port. The speaker maintains through communication with the ear canal. When the valve is not powered, direct communication with the ear canal and selected port exists. An alternative to the spool configuration shown in FIG. 7 is the spool slot isolator shown in FIGS. 12a and b.

Figure 13A:
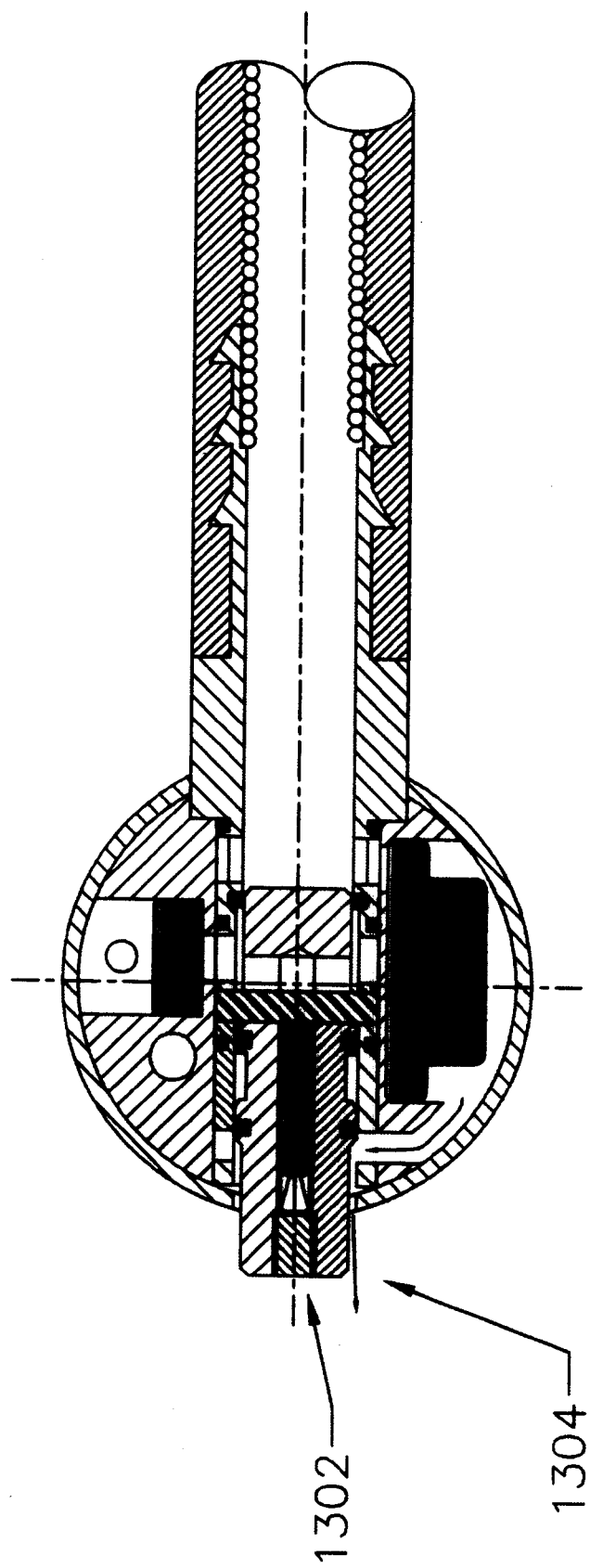
FIG. 13-A A cross-sectional view of the spool according to one embodiment of the present invention.

Referring to FIGS. 13a and b, a top view of a spool according to a fourth alternative embodiment of the present invention is shown. Referring to FIG. 13a, the spool is adapted such that when plunger 1302 is depressed, the speaker gains access to the atmosphere via port 1304. This porting arrangement provides a true compliance membrane and thus minimizes power requirements. Typically, porting to the atmosphere is desirable when the stethoscope is operated in electronic mode to optimize the efficiency of the speaker by reducing vapor lock. Moreover, in conjunction with the acoustic conduit configuration explained below, this porting arrangement enables the left and right channels to be completely separated.

Figure 13B:
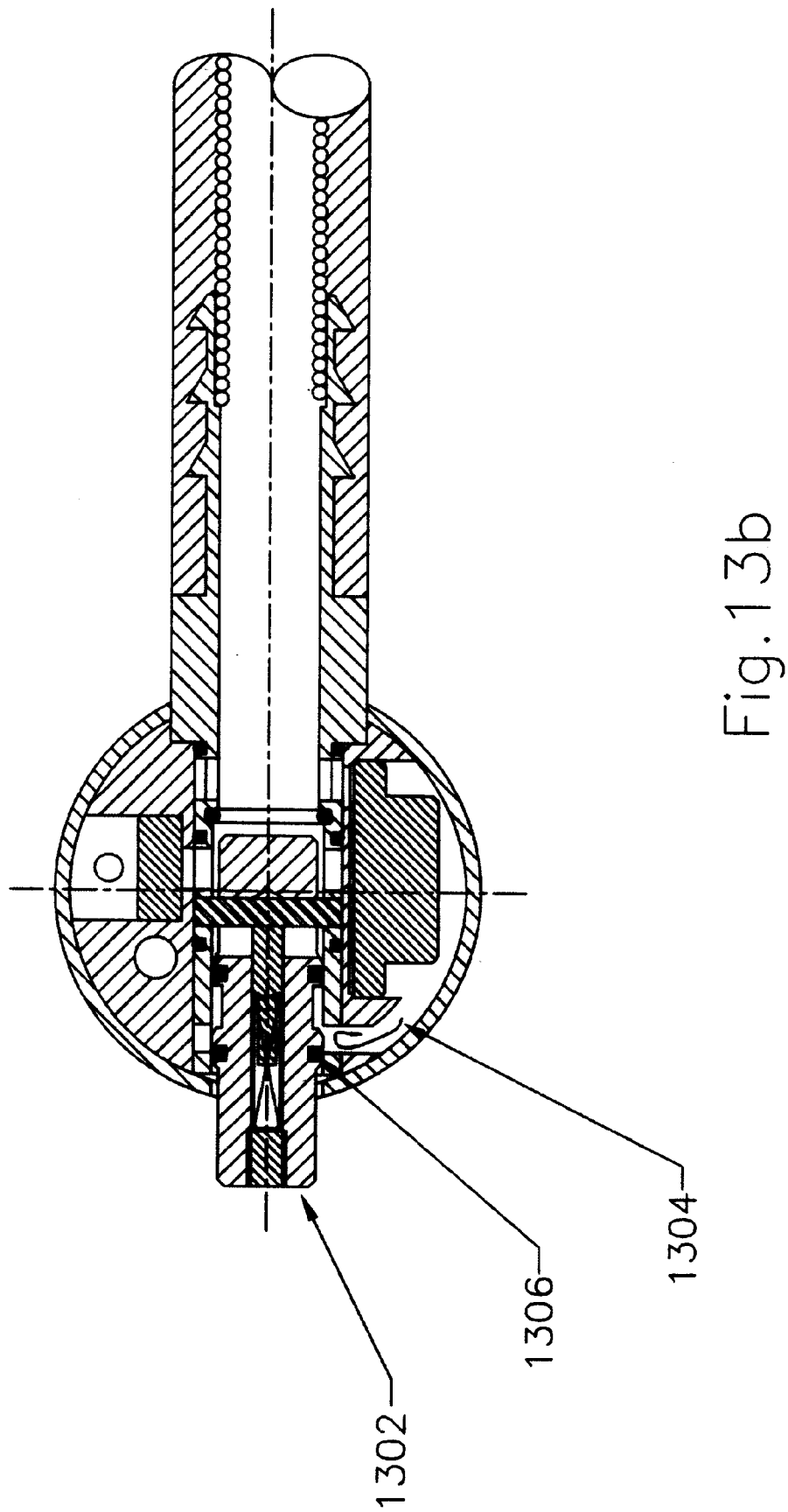

Referring to FIG. 13b, when plunger 1302 is not depressed, port 1304 is closed and a true. acoustic stethoscope is provided. Specifically, at least one O-ring 1306 is provided and forms a seal around plunger 1302 so that when plunger 1302 is not depressed, port 1304 is closed, thus eliminating any porting to the atmosphere. In alternate embodiments, plunger 1302 may be adapted such that the speaker is ported to the atmosphere when plunger 1302 is not depressed, and the speaker is sealed when plunger 1302 is depressed.

Figure 14:
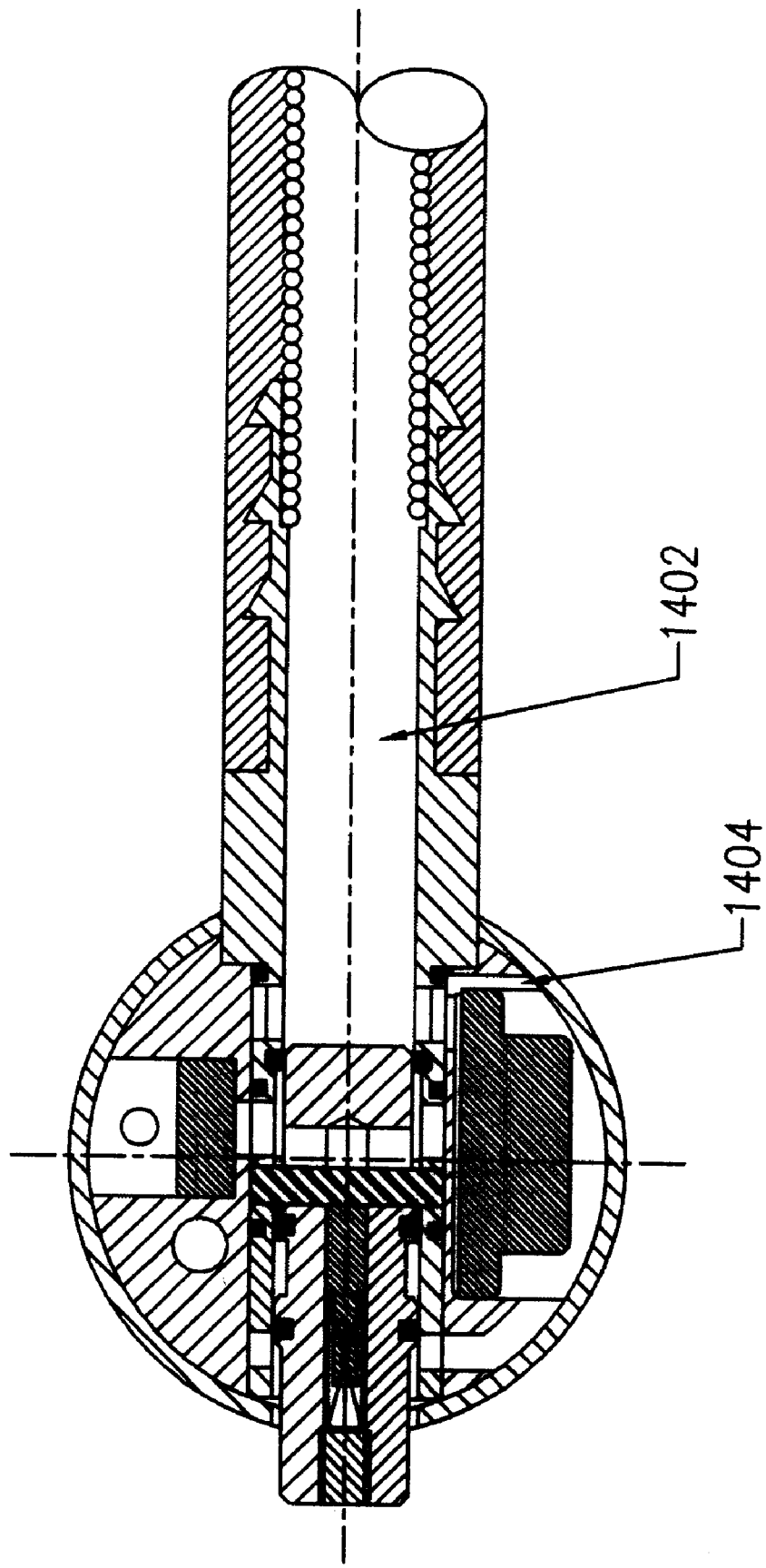
FIG. 14 A cross-sectional view of the spool according to one embodiment of the present invention.

Referring to FIG. 14, an top view of a spool according to a fifth alternative embodiment of the invention is shown. In this embodiment, an alternative to porting to the atmosphere in electronic mode is provided. In order for the speaker to operate, it needs room to work. The speaker is not ported to the atmosphere, it has to get this room to work somewhere else. The spool shown in FIG. 14 provides the speaker with room to work by porting the speaker into the acoustic conduit. Specifically, the speaker accesses the acoustic conduit through passageway 1404. The acoustic conduit acts as a false lumen 1402 providing a column of air enabling the speaker to work.

Figure 15B:
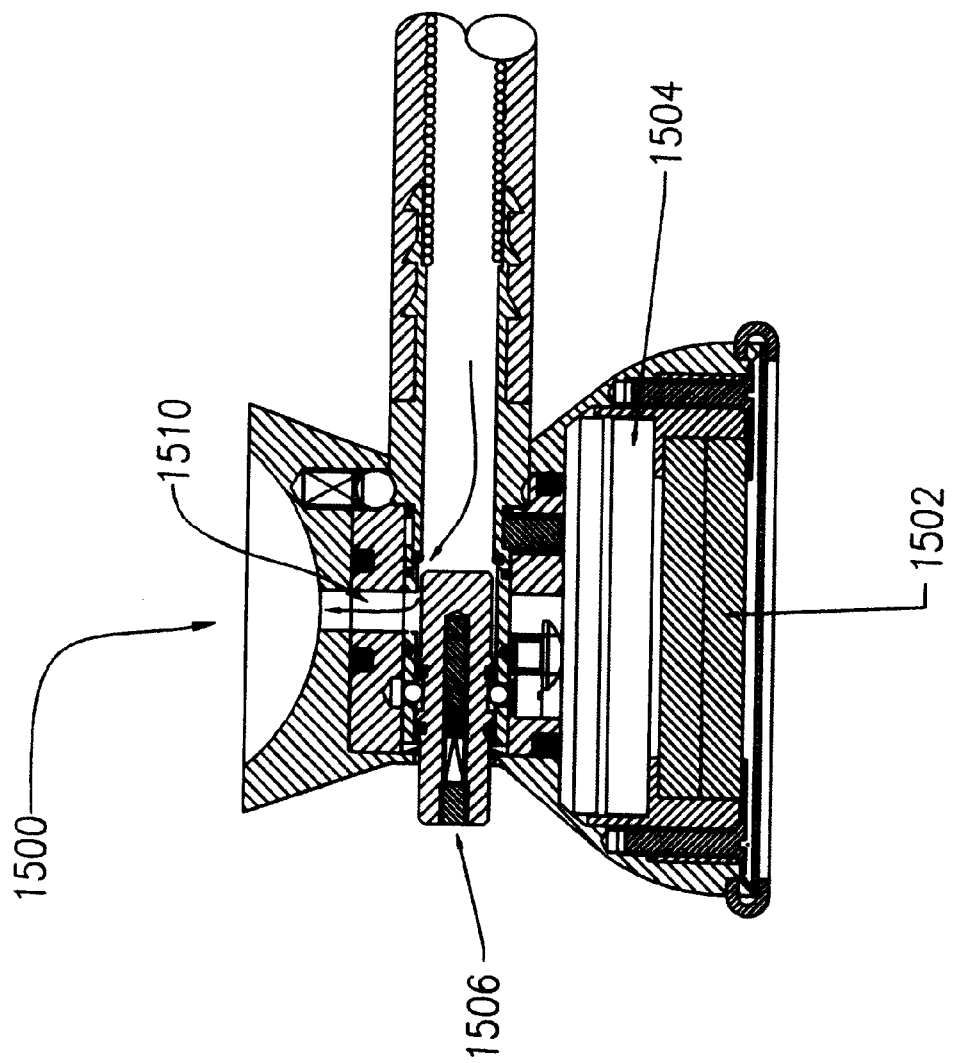
FIG. 15a A cross-sectional view of the stethoscope according to another embodiment of the present invention FIG. 15b A cross-sectional view of the stethoscope according to another embodiment of the present invention FIG. 16a–c Views of the stethoscope's full insert.
Figure 16D:
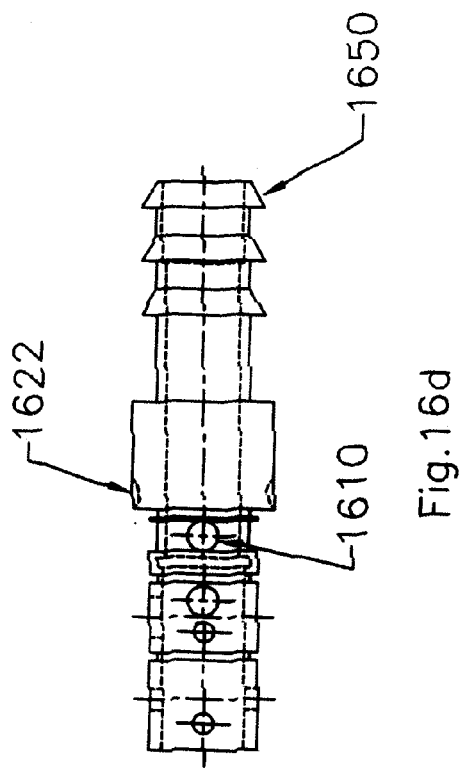
FIG. 16d–f Views of the stethoscope bar.
Figure 16F:
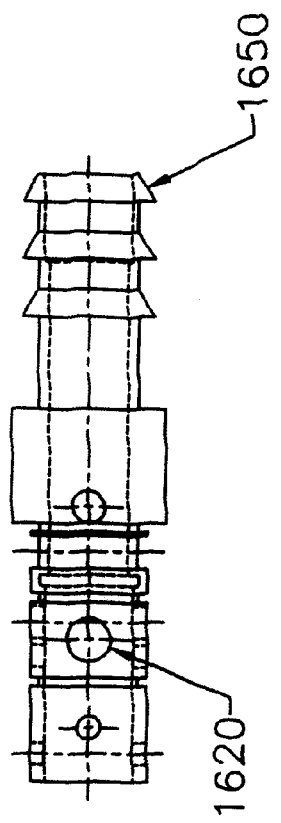
Figure 16E:
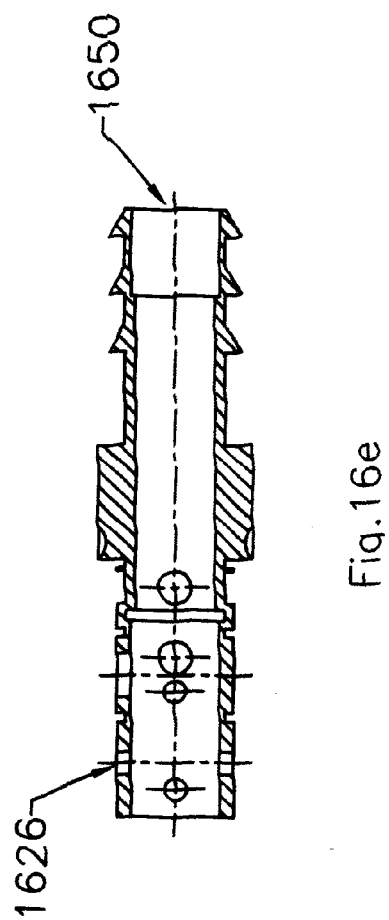
Figure 16G:
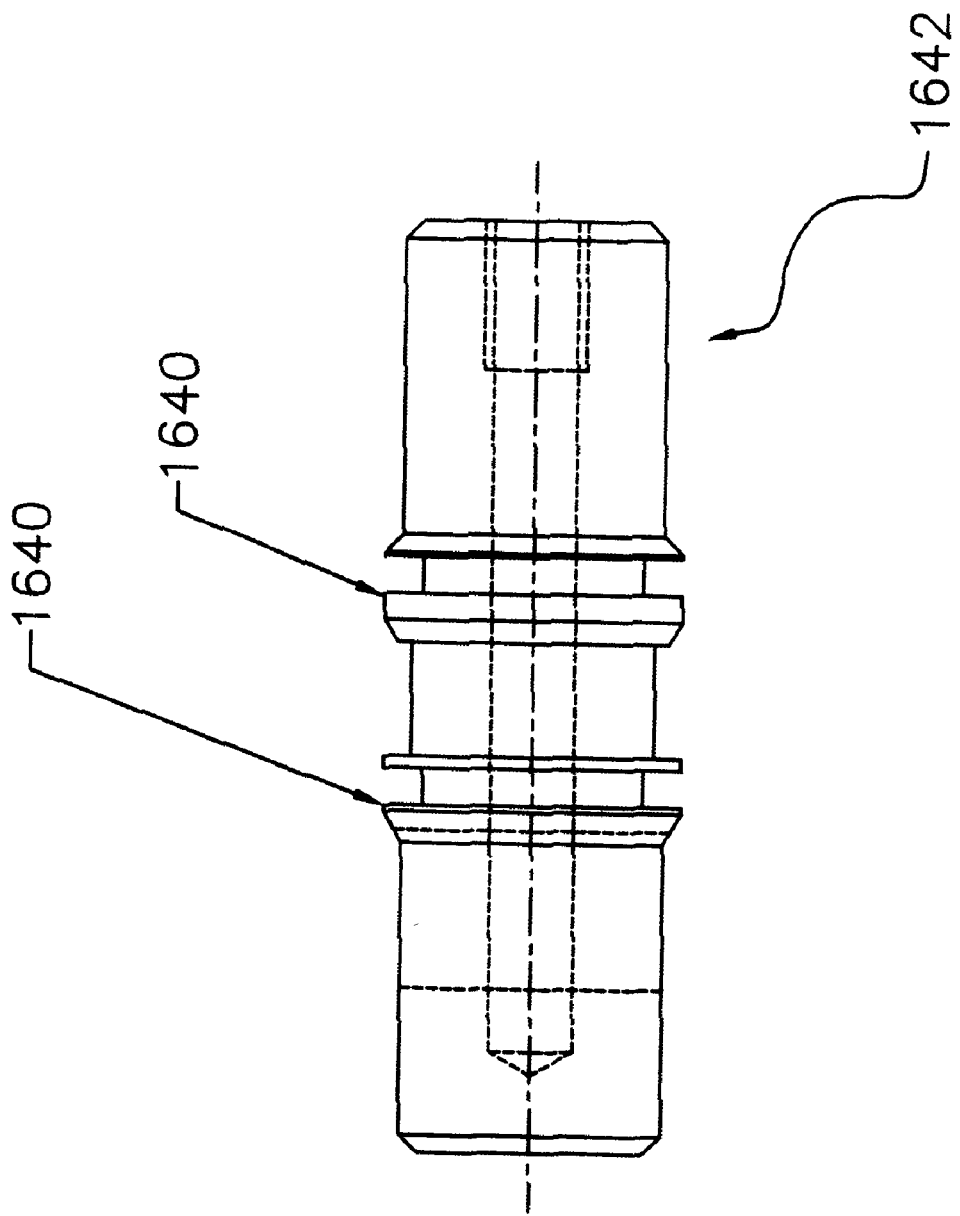
FIG. 16g View of the stethoscope plunger.

Referring to FIGS. 15a and b, a cross-sectional view of the main body of a stethoscope 1500 according to another embodiment of the present invention is shown. Stethoscope 1500 comprises battery pack 1502, internal electronics 1504, and plunger 1506. In FIG. 15a, plunger 1506 is depressed and o-ring 1508 provides a seal so that an isolation between the bell and the speaker occurs. In FIG. 15b, plunger 1056 is not depressed, and a continuous acoustic port is provided by path 1510. The direction of porting is adjustable by rotating the stethoscope head. In an alternative embodiments, the main body of the stethoscope could be configured such that the continuous acoustic port is provided when plunger 1056 is depressed.

Referring to FIGS.16a–g, the stethoscope's full insert (FIGS. 16a–c), the stethoscope bar (FIGS. 16d–f), and the stethoscope plunger (FIG. 16g) are shown. In a preferred embodiment, plunger 1642 is "out" in conventional mode. In an alternate embodiment, plunger 1642 is "in" in conventional mode. Other configurations may also be used.

Communication with the bell or diaphragm may be achieved through diaphragm through hole 1606 or bell through hole 1604. Through communication may be provided by stethoscope barb port 1620. The bell diaphragm mode may be maintained by detente engagement hole 1622. Detente engagement hole 1622 may allow for rotation of the barb 1650. In a preferred embodiment, 180° of rotation may be provided. O-ring grooves 1640 provide a seal in acoustic mode to prevent leaks to the atmosphere.

In electronic mode, plunger 1642 may be engaged such that microphone port 1608 has access to either the bell or the diaphragm, through bell through hole 1604 or diaphragm through hole 1606, respectively. In a preferred embodiment, engagement is achieved by depressing plunger 1642. In an alternate embodiment, engagement is achieved by releasing plunger 1642. Other engagement techniques may also be used.

The speaker ports to the ear canal via port 1610, the forward porting chamber. Speaker vapor lock is released through porting 1612, which ports to the atmosphere. When plunger 1642 is engaged, switch is engaged through switch detente hole 1009. Other porting configurations may also be used.

Figure 3:
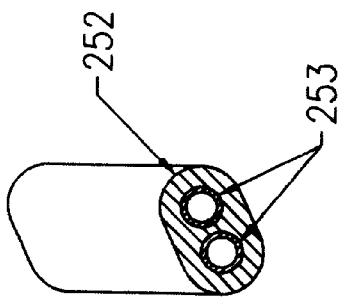
FIG. 3 A cross-sectional view of an improved stethoscope tube structure according to one embodiment of the present invention.
Figure 2:
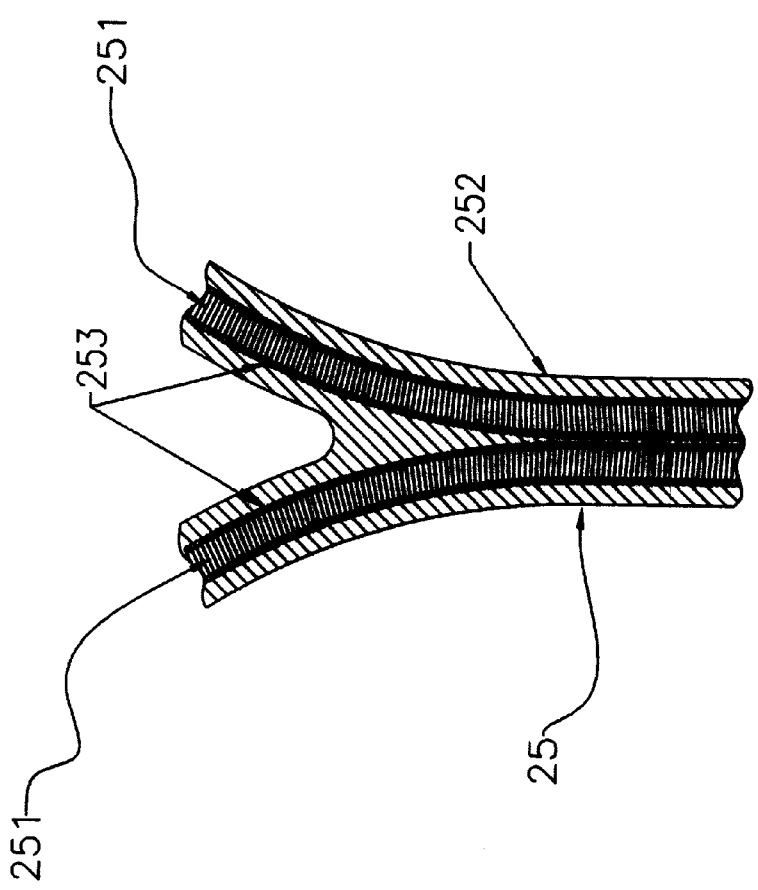
FIG. 2 A pictorial view of an improved stethoscope tube structure according to one embodiment of the present invention.

In another embodiment, the present invention comprises an acoustic conduit for use as, for example, an improved stethoscope tube 25 such as is shown in FIGS. 2 and 3. Referring to FIGS. 2 and 3, improved stethoscope tube 25 comprises an outer tube or sheath 252 surrounding two inner tubes 253. In a preferred embodiment outer tube 252 comprises a bitumen (14"–16") neoprene tube. Neoprene is used to minimize cracking and age induced stiffness related with conventional PVC and latex tubing. Neoprene is also desirable because of its non-allergenic properties. Nevertheless, in another embodiment, outer tube 252 comprises a conventional PVC or latex tube. In other embodiments, silicon and related polymers may also be used.

Inner tubes 253 define separate acoustic chambers 251 leading to ear pieces 20. Inner tubes 253 are molded into outer tube 252 and provide acoustic and mechanical advantages. Inner tubes 253 preferably comprise a coiled material having a density greater than the density of the outer tube 252. The use of a relatively hard material in comparison to the material used for outer tube 252 maximizes external noise isolation and minimizes acoustic losses. That is, the PVC and latex that are typically used for stethoscope tubes are relatively soft materials (as compared to steel) and therefore absorb a portion of the sound waves incident upon them. The stainless steel used in the preferred embodiment of the present invention provides a relatively hard surface (as compared to PVC and latex) that absorbs only a small portion of incident sound waves. The use of a relatively hard material also prevents collapsing of tube 25. The coiled configuration is utilized so that tube 25 remains bendable. According to the preferred embodiment, inner tubes 253 comprise separate stainless steel coils, e.g., stainless steel compression springs. Further, the use of compression springs for inner tubes 253 provides the additional advantage of acting to straighten tube 25 when in use thereby helping to prevent kinks that may interfere with sound transmission through tube 25. In a preferred embodiment, compression springs act as a mandrel and as a heat sink for the molding process.

In addition to isolating external noises minimizing losses, the improved structure of tube 25 described above enhances the sound waves being transmitted through acoustic chambers 251. When an elastic body is acted on by a force, such as a sound wave, it vibrates with an amplitude roughly proportional to the amplitude of the sound wave. Nevertheless, elastic bodies have certain natural frequencies of vibration which are characteristic of the material and boundary conditions. When an elastic body is acted on by a force, such as a sound wave, at or near that certain frequency (its resonant frequency), the body vibrates with an amplitude that is greater than would ordinarily be expected i.e., it resonates.

The stainless steel used for inner hard tubes 253 and the boundary between the relatively soft outer tube 252 and relatively hard inner tubes 253 maximizes this phenomenon of resonance with respect to typical body cavity sounds. Thus, when tube 25 and inner hard tubes 253 are acted on by a series of periodic impulses, e.g., body cavity sounds, that have a frequency nearly equal to the resonant frequency of the tube 25 and inner hard tubes 253, tube 25 and inner hard tubes 253 resonate. This has the effect of amplifying the body sounds transmitted through tube 25. Thus, the improved configuration of tube 25 described above maximizes the phenomenon of resonance to provide superior acoustic chambers 251. The configuration maximizes the loudness, pitch, and quality of the body cavity sounds while maintaining a flexible conduit to the ear canal.

Figure 9:
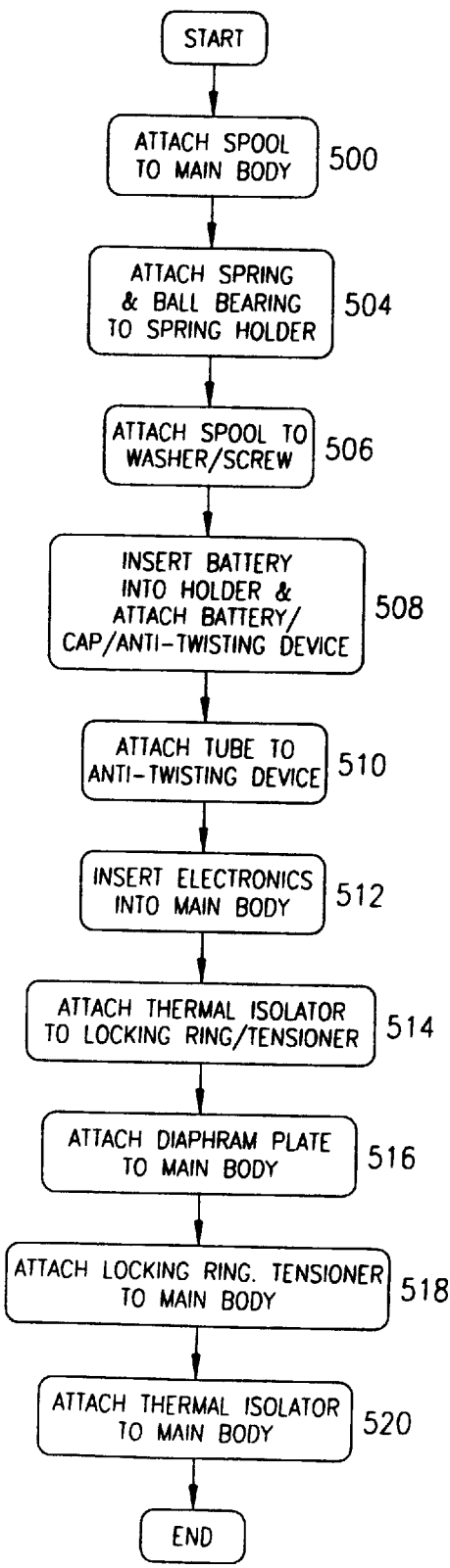
FIG. 9 A method of assembling a stethoscope according to one embodiment of the present invention.

Referring to FIG. 4 and 9, the stethoscope is assembled in a step wise sequence. Spool 90 is secured to battery holder 110. (step 500) Spool 90 with attached battery holder 110 secured into position is inserted into main body 35. (step 502) The spring 70 and stainless ball bearing 17 are placed into the spring holder (not shown). (step 504) Spool 90 is locked into position by washer 65 and screw 60. (step 506) Battery 115 is then inserted into battery holder 110 and secured into position by battery end cap 120 which is fixed to anti-twisting device 125. (step 508) Tube 25 is forced over the tapered barbed end of anti-twisting device 125. (step 510) Electronics 200 are inserted into their appropriate positions within main body 35 and secured into position. (step 512) Thermal isolator 42 is secured to locking ring/tensioner 44. (step 514) Diaphragm plate 41 is placed between the main body 35 and locking ring tensioner 44. (step 516) Once aligned, the locking ring/tensioner 44 is secured to the main body 35. (step 518) Bell thermal isolator 42 is secured to main body 35. (step 520)

FIG. 5 depicts spool 90 and main body 35 in electronic mode. FIG. 6 depicts spool 90 and main body 35 in conventional mode. FIG. 7 depicts spool 90 in greater detail. Depressing the spool opens and/or closes bell communication port 87 in bell mode or diaphragm communication port 85 in diaphragm mode allowing the classic and electronic features to coexist without feedback.

Referring to FIG. 5, electronics 200 may be constructed of standard electronic chips or a combination of miniature hardware and software or other electronics suitable for performing the necessary functions within the given space limitations. Referring to FIG. 8, band pass filter 602 isolates pathological and physiological frequencies. Sound recorder/register 610 responds to tap switch 608 which includes an off, on#1, on#2, on#3 setting, which refers to off-amplify, playback, slow playback, and record respectively. Electronics 200 adapted for recording, allows for playback/slow playback of heart sounds while maintaining classic features of passive acoustic conduction. Each new recording will erase the previous recording.

The Echo+™ utilizes a hard flexible tube and three methods of noise reduction when in the electronic mode. Through electronics 200 the user is able to physically remove him or herself from a noisy environment. After recording, in a noisy room, the user can simply move to a quiet room for playback. The second method relies on the band pass filters in electronics 200 to attenuate frequencies above 470 Hz. Speech in the range of 2000 to 4000 Hz is filtered very effectively through the band pass filter. The third method of noise reduction makes use of destructive interference and superposition principles. This feature is available only in the real-time amplify mode. Through electronics 200, two different signals are produced. Signal one, consisting of pure body cavity sounds and external noise transmitted into the body cavity is filtered and amplified. A second signal representative of the external noise is inverted, filtered, and attenuated. The two signals are then allowed to destructively interfere with one another in the acoustic chamber. The net result of the destructive interference produces a third signal that represents pure body cavity sounds, i.e. unwanted noise is removed. This improved signal is transmitted to the ear canal through the flexible hard tube. Quick connect female output jack 86 allows playback of recorded heart sounds through external speakers or transmission over telephone lines.

An embodiment of the present invention provides real time amplification in one unit that reproduces as exactly as possible at the users ear the sound pressure signals originating from a conventional diagram or bell type of chest piece.

An additional embodiment utilizes a signal processing approach which adjusts the amplifier gain control to improve diagnostic resolution. Microphone 205 detects audible sounds from patient and produces an output signal representative thereof and a variable gain amplifier 260 amplifies the output signals from microphone 205 to the speaker 210.

In another embodiment an improved conduit is used to provide an acoustic chamber. The acoustic chambers, consisting of inner hard tubes 253 and outer tubes 252, improve sound quality by providing less signal distortion and decay in signal amplitude than is typical experienced in conventional stethoscopes. Amplitude is maximized through resonance of inner hard tubes 253 and outer tube 252, thus providing less decay in amplitude than a conventional stethoscope when in conventional mode.

An additional embodiment, utilizes a slow playback mode in which the output is modulated to extend playback thus providing a slowed down version of the original sound, e.g. a slower heart beat without changing the quality of the sound as perceived by a health care provider.

Other embodiments and uses of the invention will be apparent to those of ordinary skill in the art from consideration of the specification and practice of the invention disclosed herein. All U.S. patents and other documents cited herein are hereby specifically incorporated by reference. The specification and examples should be considered exemplary only with the true scope and spirit of the invention indicated by the following claims.

What is claimed is:

1. A stethoscope comprising:

a head assembly;

a conduit assembly having a proximal end and a distal end, the proximal end of the conduit assembly connected to the head assembly, the conduit assembly comprising:

a flexible outer tube comprised of a first material, the first material having a first density;

a first inner tube independent from and disposed within the outer tube, said first inner tube comprised of a second material, said second material having a density greater than said first density; and, a second inner tube independent from and disposed within the outer tube, said second inner tube comprised of the second material, said first inner tube and said second inner tube defining a first acoustic chamber and a second acoustic chamber respectively; and, a first and a second ear piece operatively connected to the first acoustic chamber and the second acoustic chamber respectively at the distal end of the conduit assembly.

2. The stethoscope of claim 1 wherein the first material comprises a polymer.

3. The stethoscope of claim 1 wherein the first material comprises neoprene.

4. The stethoscope of claim 1 wherein the first inner tube comprises a first spring and the second inner tube comprises a second spring.

5. The stethoscope of claim 1, said head assembly comprising at least one bell communication port.

6. The stethoscope of claim 5, wherein said bell communication port is a female electrical connector for downloading internally stored data.

7. An acoustic conduit used to transmit sound from a source to a destination through a first acoustic chamber and a second acoustic chamber, the conduit comprising:

a flexible sheath comprised of a first material, the flexible sheath encasing the first acoustic chamber and the second acoustic chamber;

a first inner spring disposed within the flexible sheath and forming the first acoustic chamber; and, a second inner spring disposed within the flexible sheath and forming the second acoustic chamber.

8. The conduit of claim 7 wherein the flexible sheath is comprised of a first material having a first density;

wherein the first inner spring and the second inner spring are comprised of a second material having a second density; and, wherein the second density is greater than the first density.

9. The conduit of claim 8 wherein the first material comprises neoprene.

10. An acoustic/electronic stethoscope comprising:

a head assembly comprising:
       a speaker, the speaker generating sound when the stethoscope operates in an electronic mode; and,
       a port configured to provide the speaker with access to the atmosphere when the stethoscope operates in the electronic mode;

a conduit assembly having a proximal end and a distal end, the proximal end of the conduit assembly connected to the head assembly, the conduit assembly comprising:
       a flexible outer tube comprised of a first material, the first material having a first density;
       a first inner tube independent from and disposed within the outer tube, said first inner tube comprised of a second material, said second material having a density greater than said first density; and,
       a second inner tube independent from and disposed within the outer tube, said second inner tube comprised of the second material, said first inner tube and said second inner tube defining a first acoustic chamber and a second acoustic chamber respectively; and, a first and a second ear piece operatively connected to the first acoustic chamber and the second acoustic chamber respectively at the distal end of the conduit assembly.

11. A stethoscope comprising:

a head assembly;

a conduit assembly having a proximal end and a distal end, the proximal end of the conduit assembly connected to the head assembly, the conduit assembly comprising:
       a flexible outer tube comprised of a first material, the first material having a first density;
       a first inner tube independent from and disposed within the outer tube, said first inner tube comprising a coiled material having a density greater than said first density; and,
       a second inner tube independent from and disposed within the outer tube, said second inner tube comprising the coiled material having a density greater than said first density, said first inner tube and said second inner tube defining a first acoustic chamber and a second acoustic chamber respectively; and, a first and a second ear piece operatively connected to the first acoustic chamber and the second acoustic chamber respectively at the distal end of the conduit assembly.

* * * * *